(12) United States Patent
Caillier et al.

(10) Patent No.: US 8,608,928 B2
(45) Date of Patent: Dec. 17, 2013

(54) ELECTRICAL DETECTION AND QUANTIFICATION OF CESIUM DERIVATIVES

(75) Inventors: Laurent Caillier, Opio (FR); Jean-Pierre Simonato, Sassenage (FR)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 763 days.

(21) Appl. No.: 12/715,666

(22) Filed: Mar. 2, 2010

(65) Prior Publication Data

US 2010/0237883 A1    Sep. 23, 2010

(30) Foreign Application Priority Data

Mar. 18, 2009  (FR) .................................... 09 01253

(51) Int. Cl.
*G01N 27/333* (2006.01)
*G01N 27/414* (2006.01)

(52) U.S. Cl.
USPC .......................................... 204/418; 257/253

(58) Field of Classification Search
USPC ..................... 257/9, 20, 414, 27, 37, 72, 134; 324/694; 204/418
See application file for complete search history.

(56) References Cited

U.S. PATENT DOCUMENTS

2008/0264790 A1 * 10/2008 Kamahori et al. ............ 204/418

OTHER PUBLICATIONS

Cui et al., Science, 2001, 293, 1289-1292.*
Lugtenberg et al., Journal of Electroanalytical Chemistry, 1992, 452, 69-86.*
Lee et al., Tetrahedron Letters, 2005, 46, 8163-8167.*
Curreli et al. IEEE Transactions on Nanotechnology, 7, 2008, 651-667.*
Aramata et al., Thin Solid Films, 2003, 424, 239-246.*
E.J.R. Sudholter, P.D. van der Wal, M. Skowronska-Ptasinska, A. van den Berg, P. Bergveld, D.N. Reinhoudt, Anal. Chim. Acta 230 (1990) 59.*
P. D. van der Wal, M. Skowronska-Ptasinska, A.van den Berg, P. Bergveld, E. J. R. Sudholter, D. N. Reinhoudt, Anal. Chim. Acta 231 (1990) 41.*
Ronny J. W. Lugtenberg, et al., "Cesium-selective chemically modified field effect transistors with calix[4]arene-crown-6 derivatives", Analytica Chimica Acta vol. 310, No. 2, 1995, XP-002553589, pp. 263-267.
Jong Seung Kim, et al, "Cesium-ion selective electrodes based on calix[4]arene dibenzocrown ethers", Talanta vol. 48, No. 3, Mar. 1999, XP-002553590, pp. 705-710.
Rainer Ludwig, et al., "Calixarene-Based Molecules for Cation Recognition", Sensors, vol. 2, Oct. 2002, XP-002553591, pp. 397-416.
Lassaad Baklouti, et al., "1,3-Alternate, the Smart Conformation of Calix[4]arenes", Mini-Reviews in Organic Chemistry, vol. 3, No. 4, Nov. 2006, XP-009125186, pp. 355-384.

* cited by examiner

*Primary Examiner* — Alex Noguerola
(74) *Attorney, Agent, or Firm* — Oblon, Spivak, McClelland, Maier & Neustadt, L.L.P.

(57) ABSTRACT

The invention relates to an apparatus and to a process for the detection and/or quantification of cesium ions $Cs^+$ in solution in a liquid medium.
The apparatus of the invention comprises: a) an electrical device comprising two electrodes and a substrate comprising at least one portion made of a semiconductor material, the electrodes being in electrical contact with said semiconductor material; and b) a device for measuring the variation of the conduction current between the two electrodes, and at least one ligand comprising at least one calix[n]arene group bonded by grafting to the semiconductor material of the substrate of the electrical device or to one of the electrodes of the electrical device.
The invention finds an application in the field of the detection of cesium ions in particular.

10 Claims, No Drawings

ELECTRICAL DETECTION AND QUANTIFICATION OF CESIUM DERIVATIVES

The invention relates to an apparatus and to a process for the detection and/or quantification of cesium ions $Cs^+$.

The major source of cesium in the environment originates from nuclear waste, in which it is one of the most harmful fission products, along with strontium and the various isotopes of uranium.

Cesium-137, a β-emitter, has a long radioactive half-life of 30 years.

Absorbed by man, there is a biological period of 100 days before elimination of the element by the body.

Cesium is a very toxic element since it has the ability to replace potassium in the cells and the blood.

This property is due to the fact that potassium and cesium, and moreover cesium and sodium, have very close chemical properties.

Because of the ubiquity of $Na^+$ and $K^+$ in radioactive effluents and more generally in the environment, it is very difficult to selectively detect cesium in liquid media.

Various methods have been described for the detection of cesium such as:
  atomic absorption spectroscopy;
  radioanalysis;
  the electrochemical technique used in solution with a modified gold electrode and a reference electrode. This technique is in particular described in U.S. Pat. No. 6,924,380; and
  the use of an SAW ("Surface Acoustic Wave") system described by Pinnaduwage et al. based on the grafting of calixarene derivatives to a micro-cantilever. Specifically, calix[n]arenes are known for their heavy metal complexation properties, as described by Ikeda et al., Chem. Rev. 1997, 97, 1713-1734 and Böhmer et al. Chem., Int. Ed. Engl. 1995, 34, 713-745.

Calix[n]arenes are known macrocycles. In the name "calix[n]arene", n indicates the number of arene units in the macrocycles. These compounds are also referred to below as a "calixarene group or calix[n]arene group".

The complexation properties of calix[n]arenes result directly from the structure of the macrocyclic core of the molecule and may be adjusted by the variation of various substituents borne by this molecule.

More specifically, the derivatives of calix[4]arene type in 1,3-alternate conformation and bearing a crown-6-ether appear to be ligands specific to the cesium ion according to Guillon et al. J. Org. Chem., 2000, 65 (24) 8283-8289.

Thus, Moyer et al. proposed the specific extraction of cesium from a liquid medium by calixarene crown ethers in U.S. Pat. No. 6,174,503 B1.

However, due to their unwieldy technologies or their low selectivities, these various techniques of the prior art do not appear very suitable for the manufacture of low-cost, very small-sized sensitive sensors that require little energy in order to function.

Remarkably, the inventors have observed that the complexation of the element cesium by a ligand comprising a calix[n]arene group grafted to or in the vicinity of a semiconductor material modifies the electrostatic environment of this semiconductor material whereas a priori it might have been thought that the calix[n]arene group would have acted like a screen due to its size and its density of electrons, thus masking the induced electrostatic charge variation.

Therefore, the invention proposes an apparatus for the detection and/or quantification of cesium ions $Cs^+$ in solution in a liquid medium comprising:
  an electrical device comprising two electrodes and a substrate comprising at least one portion made of a semiconductor material, the electrodes being in electrical contact with said semiconductor material; and
  a device for measuring the variation of the conduction current between the two electrodes, wherein at least one ligand, comprising at least one calix[n]arene group and at least one grafting group, is bonded by grafting to the semiconductor material of the substrate of the electrical device or to one of the electrodes of the electrical device.

The semiconductor material is chosen from carbon-based materials, silicon-based materials, germanium-based materials, zinc-based materials, gallium-based materials, indium-based materials, cadmium-based materials or an organic semiconductor material, preferably poly(3,4-ethylenedioxythiophene)/poly-(styrenesulfonate).

As regards the electrodes, they are made of a material chosen from gold, silver, palladium, platinum, titanium, copper, nickel and carbon nanotubes.

Preferably, said at least one calix[n]arene unit is a calix[4]arene unit in 1,3-alternate, crown-6-ether conformation.

In one embodiment of the apparatus of the invention, the at least one ligand is bonded by grafting to the semiconductor material of the substrate of the electrical device, and the semiconductor material is a silicon-based material, that is to say a material comprising 20% by weight of silicon. Preferably, it is composed of unoxidized silicon nanowires and/or nanotubes. In this case, the at least one ligand comprises a grafting group chosen from an alkyne group, an alkene group or a radical precursor group such as a diazonium group and a triazonium group.

In another embodiment of the apparatus of the invention, the at least one ligand is bonded by grafting to the semiconductor material of the substrate of the electrical device, the semiconductor material of the substrate is an oxidized silicon-based material, preferably constituted of surface-oxidized silicon nanowires and/or nanotubes, and the at least one ligand comprises a grafting group chosen from a silane group, preferably a trialkoxysilane or trihalosilane group, more preferably a trimethoxysilane or trichlorosilane group.

In yet another embodiment of the apparatus of the invention, the at least one ligand is bonded to carbon nanowires and/or nanotubes and comprises a grafting group chosen from a radical precursor group such as a diazonium group, a triazonium group, an aromatic or heteroaromatic group, such as a pyrene group, an anthracene group, a porphyrin group or an amine group or an alcohol group.

In all the embodiments and variants of the invention, preferably the at least one ligand comprises, in addition, a spacer group bonded via one end to the grafting group and at the other end to the calix[n]arene group.

Preferably, in the detection apparatus of the invention, the ligand is chosen from 1,3-alternate 25,27-bis(1-pyren-1-yloxycarbonylmethoxy)calix[4]arene-crown-6 of formula I below:

Formula I

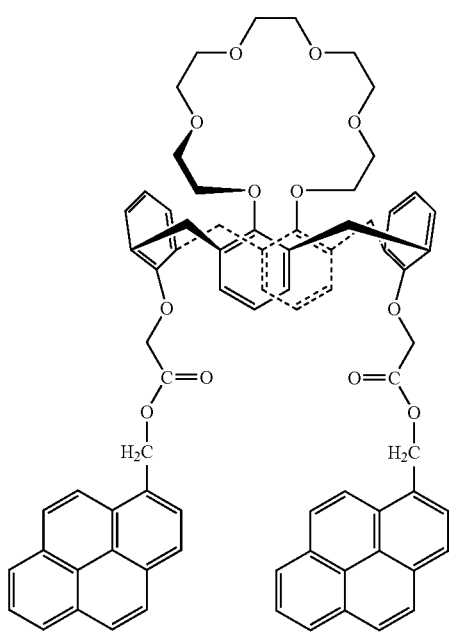

and 1,3-alternate 25,27-bis(prop-2-ynyloxycarbonyl-methoxy)calix[4]arene-crown-6 of formula II below:

Formula II

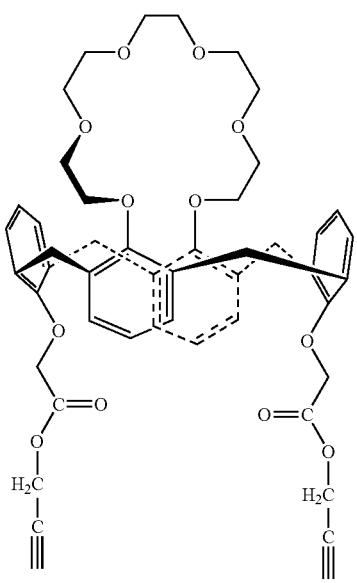

The invention also proposes a process for the detection and/or quantification of cesium ions $Cs^+$ in solution in a liquid medium, which comprises:

- contacting said liquid medium with the electrical device of the detection and/or quantification apparatus of the invention; and
- measuring the variation of the conduction current between the two electrodes of the electrical device of the detection apparatus with the device for measuring the variation of the conduction current of the apparatus of the invention.

The invention will be better understood, and other advantages and features of it will appear more clearly, on reading the explanatory description which follows.

The invention is based on the discovery that the complexation of a cesium ion by a calixarene group modifies the electrostatic environment of a semi-conductor material to which the calixarene group is grafted or in the vicinity of which it is grafted and that this variation of the electrostatic environment could be measured by an electrical device.

Since the calixarene group is a group that selectively complexes cesium ions $Cs^+$, relative to $Na^+$ and $K^+$ ions, a very selective detection and/or quantification of the cesium ion $Cs^+$ is obtained in a liquid medium with the apparatus of the invention, due, in particular, to the proximity of the calix[n]arene group and the semi-conductor material.

Preferably, the liquid medium is an aqueous medium.

Thus, in the invention, via an electrical device, the presence of at least one $Cs^+$ ion sequestered by a calixarene group, which is in the vicinity of the electrical device, is detected.

Consequently, the apparatus for the detection and/or quantification of cesium ions $Cs^+$ comprises an electrical device comprising two electrodes and a substrate comprising at least one portion made of a semiconductor material, and a device for measuring the conduction current between the two electrodes.

In order to detect and/or quantify the $Cs^+$ ions, at least one ligand comprising a calixarene group is grafted either to the semiconductor material of the substrate, or to one of the electrodes. The grafting makes it possible to obtain a detection and/or quantification apparatus that has a long service life since it makes it possible to durably maintain the calix[n]arene group on, or in the vicinity of, the semiconductor material, unlike an encapsulation of the calixarene group in a membrane which erodes during use.

The electrical device may be of resistive type or of field-effect transistor type.

The portion of the substrate made of a semiconductor material acts as a conduction channel between the two electrodes which are in electrical contact with the at least one portion made of semiconductor material.

The semiconductor material may be a material based on carbon, silicon, germanium, zinc, gallium, indium, cadmium or an organic semiconductor material such as poly(3,4-ethylenedioxythiophene)/-poly(styrenesulfonate).

Preferably, the semiconductor material is constituted of silicon nanowires and/or nanotubes or carbon nanowires and/or nanotubes.

As regards the electrodes, they may be made of gold, silver, palladium, platinum, titanium, copper or nickel, but also they may be constituted of carbon nanotubes.

In order to graft the calixarene group either to the electrode, or to the portion made of semiconductor material of the substrate of the electrical device, the ligand also comprises a grafting group which is suitable for the material to which it is grafted. This ligand will also be referred to as a calixarene ligand in what follows.

Thus, for a grafting to silicon, that is to say in the case where the semiconductor material is made of silicon or constituted of silicon nanowires and/or nanotubes, the grafting group of the ligand used in the invention is chosen from an alkyne group, an alkene group, a diazonium group, a triazine group or a radical precursor group.

This is true for all silicon-based materials.

In this regard, the expression "X-based material" is understood to mean a material comprising at least 20 mol %, relative to the total number of moles of material, of X.

When the material to which the ligand used in the invention is grafted is made of silicon but covered with a thin layer of oxide, such as native oxide for example, the grafting group is preferably chosen from a silane radical, such as a trialkoxysilane or trihalosilane radical.

Preferably, in this case, use will be made of a trimethoxysilane or trichlorosilane group.

But it will appear clearly to a person skilled in the art that any other grafting group that bonds to the surface of the oxide could be used.

Similarly, it will appear clearly to a person skilled in the art that the grafting of the calixarene ligand may be carried out in one or more steps.

Thus, it is for example possible to react the surface of the portion, made of semiconductor material, of the substrate of the electrical device of the apparatus for detection and/or quantification of $Cs^+$ ions of the invention with a first molecule, and to then react a group of this molecule grafted to the surface of the semiconductor material with an organic molecule comprising the calixarene group itself.

For example, the silicon or its native oxide will be able to be functionalized by a first series of organic molecules comprising terminal functional groups to which the ligand will be subsequently grafted via the conventional techniques of organic, organometallic or inorganic synthesis.

When the ligand is grafted to a semiconductor material based on carbon or constituted of carbon, such as for example carbon nanotubes, the grafting group will be chosen from a radical precursor group such as a diazonium group, a triazonium group or else from any molecule capable of forming covalent bonds with the carbon atoms, an aromatic or heteroaromatic group such as, for example, a pyrene group, an anthracene group, a porphyrin group or an amine group or an alcohol group for a reaction with the carboxylic acids present at the surface of the carbon, optionally after chemical inactivation, for example with a coupling agent, for ester or amide formation.

Advantageously, in the apparatus for detection and/or quantification of $Cs^+$ ions according to the invention, the ligand used in the detection apparatus of the invention comprises, besides the grafting group dedicated to the grafting of the calixarene group to the semiconductor material or to the electrodes, a spacer portion which makes it possible to adjust the distance between the calixarene group itself and the semiconductor material or the electrodes.

This spacer may be a linear $C_1$ to $C_{20}$ alkyl chain, possibly containing one or more heteroatoms, such as O, S and N and/or an aromatic radical such as a benzyl group, and/or a heteroaromatic radical such as a furan group or a pyridine group.

The structure of the apparatus obtained is simple, and allows a low-cost and large-scale production.

Furthermore, due to this simple structure, the apparatus may be of very small size, requiring little energy in order to function and favoring its portability.

With the apparatus of the invention, it is possible to detect, selectively and with sensitivity, $Cs^+$ ions in a liquid medium, in particular an aqueous medium, and also to quantify the $Cs^+$ ions by a simple calibration of the electrical device that makes it possible to link the value of the variation of the conduction current passing through the semiconductor material between the two electrodes and the concentration of calibration solution containing known amounts of $Cs^+$ ions.

Thus, the process for detecting and/or quantifying the $Cs^+$ ions according to the invention comprises a step of bringing the sample liable to contain $Cs^+$ ions into contact with the electrical device of the apparatus of the invention and the measurement of the variation of the conduction current that occurs during this bringing into contact with the device for measuring the conduction current of the apparatus of the invention.

In order to make the invention better understood, several embodiments will now be described, in a purely illustrative and non-limiting manner.

EXAMPLE 1

Resistive Sensor Based on a Mat of Functionalized Single-Walled Carbon Nanotubes (SWCNTs)

Electrical Device:

The substrate is an $Si/SiO_2$ wafer. The interdigitated electrodes (W=10 000 nm and L=50 nm) used are constituted of a stack of layers of titanium (5 nm) and of gold (30 nm).

Synthesis of the Receiver:

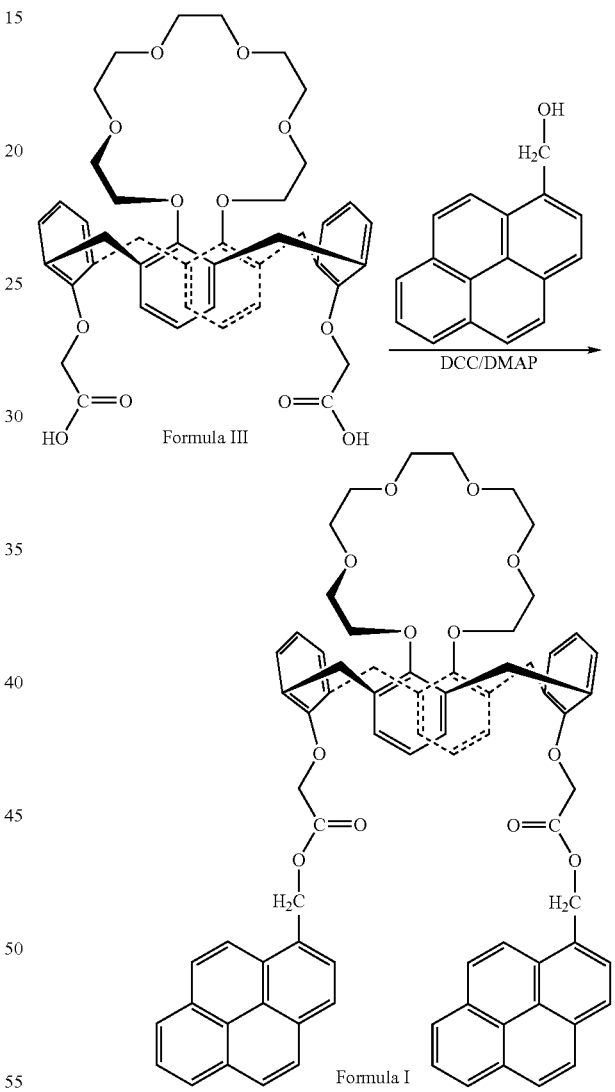

Reacted in dichloromethane is one equivalent of the compound of formula III, according to the procedure described by Guillon et coll. (J. Org. Chem., 2000, 65, 24) with two equivalents of 1-pyrenemethanol in the presence of two equivalents of dicyclohexylcarbodiimide (DCC) and a catalytic amount of 4-dimethylaminopyridine (DMAP). After treatment and purification, the compound of formula I is obtained with a yield of greater than 20%.

Manufacture of the Sensor:

The first step of manufacture consists in depositing on the device, by spraying using an airbrush, a homogeneous mat of SWCNTs between the electrodes.

In a second step, the layer of nanotubes deposited is functionalized in solution (1 mmol/l) by the receiver of formula I.

EXAMPLE 2

Test of the Sensors from Example 1

Each test device is immersed in a solution containing $Cs^+$ ions at a concentration of 1 mmol/l, then rinsed with deionized water. The device is then dried in air for 5 min. The complexation of the $Cs^+$ ions to its specific ligands leads to a modification of the resistance of the device. A relative variation of the resistance of the device |ΔAR/R| of greater than 10% was measured.

EXAMPLE 3

Sensor Based on a Pseudo-MOS Transistor

Electrical Device:
The transistor was manufactured on SOI (silicon on insulator) where the semiconductor material is an etched silicon nanowire having a width of 280 nm, a length of 4 μm and a thickness of 16 nm etched on a layer of silicon oxide of 77 nm.
Synthesis of the Receiver:

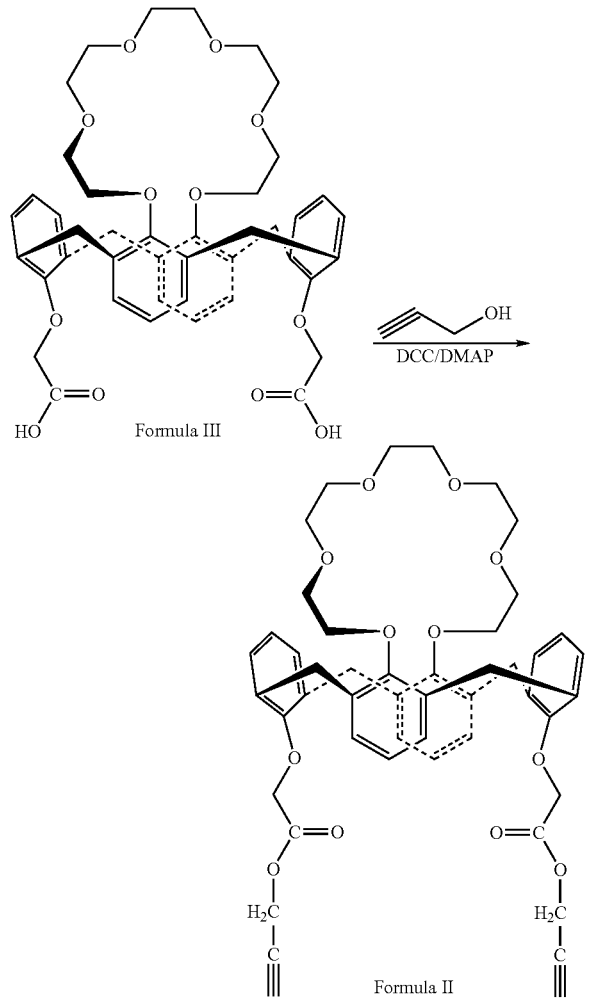

Reacted in dichloromethane is one equivalent of the compound of formula III, according to the procedure described by Guillon et coll. (J. Org. Chem., 2000, 65, 24) with two equivalents of propargyl alcohol in the presence of two equivalents of dicyclohexylcarbodiimide (DCC) and a catalytic amount of 4-dimethylaminopyridine (DMAP). After treatment and purification, the receiver of formula II is obtained with a yield of greater than 20%.

Manufacture of the Sensor:
The receiver of formula II is grafted to the test device via thermal hydrosilylation. The device is cleaned using a piranha solution then treated with a 1% HF solution. The activated device is heated at reflux for 2 hours in a 0.5 mM solution of the receiver in mesitylene. The device is then rinsed with dichloro-methane.

EXAMPLE 4

Test of the Sensors from Example 2

Each test device is immersed in a solution containing $Cs^+$ ions at a concentration of 1 mmol/l then rinsed with deionized water. The device is then dried in air for 5 min. A modification of the response of the transistor with a threshold voltage shift of 3 V is evidenced.

The invention claimed is:

1. A detection apparatus for the detection and/or quantification of cesium ions $Cs^+$ in solution in a liquid medium comprising:
   an electrical device comprising two electrodes and a substrate comprising at least one portion made of a semiconductor material, the electrodes being in electrical contact with said semiconductor material; and
   a device for measuring the variation of the conduction current between the two electrodes,
   wherein at least one ligand comprising at least one calix[n]arene group and at least one grafting group is bonded by grafting to the semiconductor material of the substrate of the electrical device or to one of the electrodes of the electrical device.

2. The detection apparatus as claimed in claim 1, wherein the semiconductor material is chosen from carbon-based materials, silicon-based materials, germanium-based materials, zinc-based materials, gallium-based materials, indium-based materials, cadmium-based materials or an organic semiconductor material, including poly(3,4-ethylenedioxythiophene)/poly(styrenesulfonate).

3. The detection apparatus as claimed in claim 1 or 2, wherein the electrodes are made of a material chosen from gold, silver, palladium, platinum, titanium, copper, nickel and carbon nanotubes.

4. The detection apparatus as claimed in claim 1, wherein said at least one calix[n]arene unit is a calix[4]arene unit in 1,3-alternate, crown-6-ether conformation.

5. The detection apparatus as claimed in claim 1, wherein:
   the at least one ligand is bonded by grafting to the semiconductor material of the substrate of the electrical device;
   the semiconductor material of the substrate of the electrical device is a silicon-based material, including at least one of unoxidized silicon nanowires and nanotubes,
   and wherein:
   the at least one ligand comprises a grafting group chosen from an alkyne group, an alkene group, a diazonium group or a triazonium group.

6. The detection apparatus as claimed in claim 1, wherein:
   the at least one ligand is bonded by grafting to the semiconductor material of the substrate of the electrical device;
   the semiconductor material of the substrate of the electrical device is an oxidized silicon-based material, including at least one of surface-oxidized silicon nanowires and nanotubes, and wherein:

the at least one ligand comprises a grafting group chosen from a silane group, being one of a trialkoxysilane group, trihalosilane group, a trimethoxysilane group, and trichlorosilane group.

7. The detection apparatus as claimed in claim 1, wherein the at least one ligand is bonded by grafting to carbon nanowires and/or nanotubes and wherein the ligand comprises a grafting group chosen from a diazonium group, a triazonium group, a pyrene group, an anthracene group, a porphyrin group, an amine group an alcohol group.

8. The detection apparatus as claimed in claim 1, wherein the at least one ligand comprises, in addition, a spacer group bonded via one end to the grafting group and at the other end to the calix[n]arene group.

9. The detection apparatus as claimed in claim 1, wherein the ligand is chosen from 1,3-alternate 25,27-bis(1-pyren-1-yloxycarbonyl-methoxy)calix[4]arene-crown-6 of formula I below:

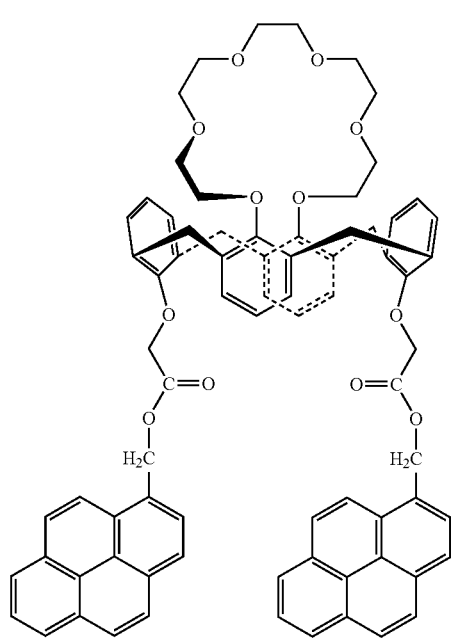

Formula I and 1,3-alternate 25,27-bis(prop-2-ynyloxycarbonyl-methoxy)calix[4]arene-crown-6 of formula II below:

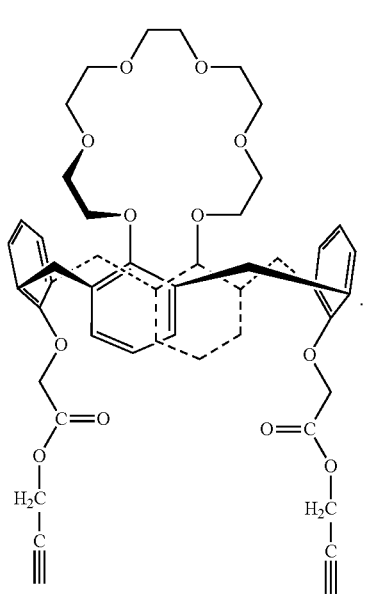

Formula II

10. A process for the detection and/or quantification of cesium ions $Cs^+$ in solution in a liquid medium, which comprises:

bringing said liquid medium into contact with the electrical device of the detection apparatus as claimed in claim 1; and measuring the variation of the conduction current between the two electrodes of the electrical device with the device for measuring the variation of the conduction current of the detection apparatus as claimed in claim 1.

* * * * *